US008871056B2

(12) United States Patent
Gane et al.

(10) Patent No.: US 8,871,056 B2
(45) Date of Patent: *Oct. 28, 2014

(54) PROCESS FOR THE PRODUCTION OF NANO-FIBRILLAR CELLULOSE GELS (75) Inventors: Patrick A. C. Gane, Rothrist (CH); Joachim Schoelkopf, Killwangen (CH); Daniel Gantenbein, Basel (CH); Michel Schenker, Oftringen (CH)

(73) Assignee: Omya International AG, Oftringen (CH)

( * ) Notice: Subject to any disclaimer, the term of this patent is extended or adjusted under 35 U.S.C. 154(b) by 46 days.

This patent is subject to a terminal disclaimer.

(21) Appl. No.: 13/138,646

(22) PCT Filed: Mar. 30, 2010

(86) PCT No.: PCT/EP2010/054233
§ 371 (c)(1),
(2), (4) Date: Oct. 14, 2011

(87) PCT Pub. No.: WO2010/115785
PCT Pub. Date: Oct. 14, 2010

(65) Prior Publication Data
US 2012/0107480 A1 May 3, 2012

Related U.S. Application Data (60) Provisional application No. 61/212,073, filed on Apr. 6, 2009.

(30) Foreign Application Priority Data

Mar. 30, 2009 (EP) .................................... 09156703

(51) Int. Cl.
*D21H 21/20* (2006.01)
*D21C 9/00* (2006.01)
(Continued)

(52) U.S. Cl.
CPC ................ *D01D 5/423* (2013.01); *D21C 9/007* (2013.01); *C08J 3/075* (2013.01);
(Continued)

(58) Field of Classification Search
USPC ............................... 524/35; 162/181.1, 181.2
See application file for complete search history.

(56) References Cited

U.S. PATENT DOCUMENTS 2,169,473 A  8/1939 Olsen
2,583,548 A * 1/1952 Lutton ........................ 162/181.2
(Continued)

FOREIGN PATENT DOCUMENTS

CA   2 437 616 A1   2/2005
EP     0726356 A1   8/1996
(Continued)

OTHER PUBLICATIONS

Campinhos, Jr. E., "Sustainable plantations of high-yield Eucalyptus trees for production of fiber: the Aracruz case." New Forests, 1999, 17, 129-143.*

(Continued)

*Primary Examiner* — Liam J Heincer
*Assistant Examiner* — Nicholas Hill
(74) *Attorney, Agent, or Firm* — Amster, Rothstein & Ebenstein LLP (57) ABSTRACT The present invention relates to a process for the production of nano-fibrillar cellulose gels by providing cellulose fibers and at least one filler and/or pigment; combining the cellulose fibers and the at least one filler and/or pigment; and fibrillating the cellulose fibers in the presence of the at least one filler and/or pigment until a gel is formed, as well as the nano-fibrillar cellulose gel obtained by this process and uses thereof.

27 Claims, 8 Drawing Sheets (51) Int. Cl.

| | | |
|---|---|---|
| C08J 3/075 | (2006.01) | |
| B82Y 30/00 | (2011.01) | |
| C08J 5/00 | (2006.01) | |
| D01D 5/42 | (2006.01) | |
| D21B 1/30 | (2006.01) | |
| C08J 3/00 | (2006.01) | |
| D21B 1/04 | (2006.01) | |
| D01F 2/00 | (2006.01) | |

(52) U.S. Cl.
CPC ............... *D21C 9/004* (2013.01); *B82Y 30/00* (2013.01); *C08J 5/005* (2013.01); *D21B 1/30* (2013.01); *C08J 3/00* (2013.01); *D21B 1/04* (2013.01); *D01F 2/00* (2013.01)
USPC .................. 162/181.1; 162/181.2; 524/35

(56) References Cited

U.S. PATENT DOCUMENTS

| | | | |
|---|---|---|---|
| 3,730,830 A | | 5/1973 | Driscoll |
| 3,794,558 A | | 2/1974 | Back |
| 4,087,317 A | | 5/1978 | Roberts |
| 4,374,702 A | | 2/1983 | Turbak et al. |
| 4,426,258 A | * | 1/1984 | Browning ............ 162/23 |
| 4,474,949 A | | 10/1984 | Chatterjee et al. |
| 4,481,076 A | | 11/1984 | Herrick |
| 4,481,077 A | | 11/1984 | Herrick |
| 4,495,245 A | | 1/1985 | Zunker |
| 4,952,278 A | | 8/1990 | Gregory et al. |
| 5,156,719 A | * | 10/1992 | Passaretti ............ 162/158 |
| 5,531,821 A | | 7/1996 | Wu |
| 5,964,983 A | | 10/1999 | Dinand et al. |
| 6,074,524 A | | 6/2000 | Wu et al. |
| 6,117,474 A | | 9/2000 | Kamada et al. |
| 6,159,335 A | | 12/2000 | Owens et al. |
| 6,183,596 B1 | | 2/2001 | Matsuda et al. |
| 6,214,163 B1 | | 4/2001 | Matsuda et al. |
| 6,436,232 B1 | | 8/2002 | Silenius et al. |
| 6,468,393 B1 | | 10/2002 | Small et al. |
| 7,381,294 B2 | | 6/2008 | Suzuki et al. |
| 7,462,232 B2 | | 12/2008 | Tuason et al. |
| 8,012,573 B2 | | 9/2011 | Kowata et al. |
| 8,231,764 B2 | | 7/2012 | Husband et al. |
| 2001/0045264 A1 | | 11/2001 | Rheims et al. |
| 2004/0108081 A1 | | 6/2004 | Hughes |
| 2004/0131854 A1 | | 7/2004 | Aho et al. |
| 2004/0168783 A1 | | 9/2004 | Munchow |
| 2005/0116010 A1 | | 6/2005 | Gronroos et al. |
| 2008/0023161 A1 | | 1/2008 | Gather |
| 2008/0060774 A1 | | 3/2008 | Zuraw et al. |
| 2008/0146701 A1 | | 6/2008 | Sain et al. |
| 2010/0272938 A1 | | 10/2010 | Mitchell et al. |
| 2010/0272980 A1 | | 10/2010 | Kowata et al. |
| 2011/0186252 A1 | | 8/2011 | Subramanian et al. |
| 2011/0259537 A1 | | 10/2011 | Husband et al. |
| 2011/0274908 A1 | | 11/2011 | Kowata et al. |
| 2011/0277947 A1 | | 11/2011 | Hua et al. |
| 2012/0043039 A1 | | 2/2012 | Paltakari et al. |
| 2012/0094953 A1 | | 4/2012 | Gane et al. |
| 2012/0107480 A1 | | 5/2012 | Gane et al. |
| 2012/0125547 A1 | | 5/2012 | Akai et al. |
| 2012/0132383 A1 | | 5/2012 | Laine et al. |
| 2012/0216718 A1 | | 8/2012 | Berglund et al. |
| 2012/0277351 A1 | | 11/2012 | Yano et al. |
| 2012/0318471 A1 | | 12/2012 | Turkki et al. |
| 2013/0053454 A1 | | 2/2013 | Heiskanen et al. |
| 2013/0126112 A1 | | 5/2013 | Gane et al. |
| 2013/0133848 A1 | | 5/2013 | Heijnesson-Hultén et al. |
| 2013/0180680 A1 | | 7/2013 | Axrup et al. |
| 2013/0284387 A1 | | 10/2013 | Umemoto et al. |
| 2013/0345416 A1 | | 12/2013 | Laukkanen et al. |
| 2014/0058077 A1 | | 2/2014 | Laukkanen et al. |

FOREIGN PATENT DOCUMENTS

| | | |
|---|---|---|
| EP | 0949294 A1 | 10/1999 |
| EP | 0852588 | 1/2003 |
| EP | 1538257 | 6/2005 |
| EP | 2236545 A1 | 10/2010 |
| EP | 2236664 A1 | 10/2010 |
| GB | 663 621 | 12/1951 |
| JP | 2007262594 A | 10/2007 |
| TW | 200609278 | 3/2006 |
| WO | WO 9856860 A2 * | 12/1998 |
| WO | WO 02/090651 A1 | 11/2002 |
| WO | WO 03/033815 A2 | 4/2003 |
| WO | 2010015726 A1 | 2/2010 |
| WO | 2010092239 A1 | 8/2010 |
| WO | 2010115785 | 10/2010 |
| WO | WO2010112519 | 10/2010 |
| WO | 2010131016 A2 | 11/2010 |
| WO | 2011134938 A1 | 11/2011 |
| WO | 2011134939 A1 | 11/2011 |

OTHER PUBLICATIONS

Auad, M. L., et al., "Characterization of nanocellulose-reinforced shape memory polyurethanes," Polymer International, 2008, 57, 651-659. Online Publication Date: Dec. 13, 2007.*
Kenny, M., et al., "Lime and Limestone," Ullmann's Encyclopedia of Industrial Chemistry. 2012. vol. 21, 37-69.*
Falini, G., et al., "Oriented Cyrstallization of Vaterite in Collagenous Matrices," Chem. Eur. J., 1998, 4, 1048-1052.*
Hubbe "Mini-Encyclopedia of Papermaking Wet-end Chemistry: Fibrillation." NC State University Internet Citation page 1.
Hubbe et al. "What Happens to Cellulosic Fibers During Papermaking and Recycling? A Review." BioResources 3(4) 739-788.
Siró et al. "Microfibrillated Cellulose and New Nanocomposite Materials: A Review." Cellulose (2010) 17:459-494.
The International Search Report dated Aug. 17, 2010 for PCT Application No. PCT/EP2010/054233.
The Written Opinion of the International Searching Authority for PCT Application No. PCT/EP2010/054233.
Third Party Observations dated Oct. 21, 2011 for European Application No. EP 09156703.2.
The European Search Report dated Jun. 26, 2009 for European Application No. EP 09156703.2.
SIXTA "Handbook of Pulp." Wood Structure and Morphology, vol. 1, pp. 41 and 42.
The Office Action dated Sep. 24, 2012 for European Application No. 10711 423.3-2115.
The Office Action dated Jan. 16, 2013 for Chinese Application No. 201080015262.5.
Little et al. "Hydrated Lime—more than just a filler." National Lime Association.
Third Party Observations dated Jun. 11, 2012 for European Application No. 10161166.3.
Communication from the European Patent Office dated Aug. 6, 2013 for European Application No. 11716257.8.
Response to the Communication dated Nov. 5, 2013 or European Application No. 11716257.8.
Third Party Observations dated May 18, 2011 for European Application No. 09156683.6.
Third Party Observations dated Jan. 9, 2012 for European Application No. 10161173.9.
Third Party Observations dated Jun. 11, 2012 for European Application No. 10161173.9.
Third Party Observations dated Apr. 12, 2013 for European Application No. 10161173.9.
European Search Report dated Jun. 26, 2009 for European Application No. EP 09156683.6.
International Search Report dated Nov. 3, 2011 for PCT Application No. PCT/EP2011/056540.
Written Opinion of the International Searching Authority dated Oct. 27, 2012 for PCT Application No. PCT/EP2011/056540.
Office Action dated Jan. 28, 2014 for Japanese Application No. 2012-502646.

(56) References Cited

OTHER PUBLICATIONS

Examination Report dated Feb. 11, 2014 for Taiwanese Application No. 099109562.
First Office Action dated Oct. 23, 2013 for Chinese Application No. 201080015263.x.
Office Action dated Mar. 30, 2010 for Russian Application No. 2011143811.
Office Action for Russian Application No. 2011143854.
Office Action dated Jan. 7, 2014 for Canadian Application No. 2,755,495.
Office Action for Ukrainian Application No. a 2011 12682.
Third Party Observation dated Jun. 6, 2012 for European Application No. 09156683.6.
Third Party Observation dated Oct. 21, 2011 for European Application No. 09156683.6.
European Search Report dated Jun. 26, 2009 for European Application No. 09156683.6.
European Search Opinion dated Jun. 26, 2009 for European Application No. 09156683.6.
Third Party Observation dated Jun. 6, 2012 for European Application No. 09156703.2.
Third Party Observation dated May 18, 2011 for European Application No. 09156703.2.
European Search Opinion dated Jun. 26, 2009 for European Application No. 09156703.2.
European Search Report dated Jun. 26, 2009 for European Application No. 09156703.2.
International Search Report dated Oct. 7, 2010 for PCT Application No. PCT/EP2010/054231.
Written Opinion of the International Searching Authority dated Sep. 30, 2011 for PCT Application No. PCT/EP2010/054231.
Shen et al. "Carbohydrate-based fillers and pigments for papermaking: A Review", 2011—Carbohydrate Polymers vol. 85, 17-22.
Chauhan et al. "Use of Nanotechnology for high performance cellulosic and papermaking products", 2002, Cellulose Chemistry and Technology, 46 (5-6), pp. 389-400.
Charani et al. "Rheological characterization of high concentrated MFC get from kenaf unbleached pulp", 2013, Celulose, vol. 20, pp. 727-740.
Opietnik et al. Tencel® Gel—A novel Cellulose Micro Suspension, 2013, Lenzinger Berichte, vol. 91, pp. 89-92.
Third Party Observations dated Jun. 11, 2012 for European Application No. EP 10713884.4.
Third Party Observations dated Feb. 17, 2012 for European Application No. EP 10713884.4.
Third Party Observations dated Jun. 11, 2012 for European Application No. EP 10711423.3.
Third Party Observations dated Feb. 17, 2012 for European Application No. EP 10711423.3.
Third Party Observations dated Jan. 9, 2012 for European Application No. EP 10161166.3.
Third Party Observations dated Apr. 12, 2013 for European Application No. EP 10161166.3.
Third Party Observations dated Feb. 4, 2013 for European Application No. EP 11716257.
Third Party Observations dated Feb. 4, 2013 for European Application No. EP 11719499.
Office Action dated Jan. 2, 2014 for European Application No. 10713884.4.
Office Action dated Feb. 21, 2013 for European Application No. 10713884.4.
Office Action dated Jan. 2, 2014 for European Application No. 09156683.6.
Office Action dated Jul. 31, 2013 for European Application No. 09156683.6.
Office Action dated Feb. 7, 2013 for European Application No. 09156683.6.
Office Action dated Jun. 27, 2011 for European Application No. 09156683.6.
Office Action dated Jul. 31, 2013 for European Application No. 09156703.2.
Office Action dated Feb. 7, 2013 for European Application No. 09156703.2.
Office Action dated May 20, 2011 for European Application No. 09156703.2.
Office Action dated Mar. 26, 2014 for European Application No. 10711423.3.
Office Action dated Sep. 24, 2012 for European Application No. 10711423.3.
Office Action dated Mar. 15, 2013 for European Application No. 10161166.3.
European Search Report dated Sep. 8, 2010 for European Application No. 10161166.3.
Office Action dated Aug. 6, 2013 for European Application No. 11716257.
Office Action dated Feb. 15, 2013 for European Application No. 11716257.
Office Action dated Mar. 15, 2013 for European Application No. 10161173.9.
European Search Report dated Sep. 7, 2010 for European Application No. 10161173.9.
Office Action dated Oct. 11, 2013 for European Application No. 11719499.

* cited by examiner

PROCESS FOR THE PRODUCTION OF NANO-FIBRILLAR CELLULOSE GELS

This is a U.S. national phase of PCT Application No. PCT/EP2010/054233, filed Mar. 30, 2010, which claims priority to European Patent Application No. 09156703.2, filed Mar. 30, 2009 and U.S. Provisional Application No. 61/212,073 filed Apr. 6, 2009.

The present invention relates to a process for producing nano-fibrillar cellulose gels and the nano-fibrillar cellulose gels obtained by this process.

Cellulose is the structural component of the primary cell wall of green plants and is the most common organic compound on Earth. It is of high interest in many applications and industries.

Cellulose is the major constituent of paper and cardboard and of textiles made from cotton, linen, and other plant fibres. Cellulose can be converted into cellophane, a thin transparent film, and into rayon, an important fibre that has been used for textiles since the beginning of the 20th century. Both cellophane and rayon are known as "regenerated cellulose fibres".

Cellulose fibres are also used in liquid filtration, to create a filter bed of inert material. Cellulose is further used to make hydrophilic and highly absorbent sponges.

For industrial use, cellulose is mainly obtained from wood pulp and cotton. It is mainly used to produce cardboard and paper; and to a smaller extent it is converted into a wide variety of derivative products.

Cellulose pulp as a raw material is processed out of wood or stems of plants such as hemp, linen and manila. Pulp fibres are built up mainly from cellulose and other organic components (hemicellulose and lignin). The cellulose macromolecules (composed of 1-4 glycosidic linked β-D-Glucose molecules) are linked together by hydrogen bonds to form a so called primary fibril (micelle) which has crystalline and amorphous domains. Several primary fibrils (around 55) form a so called microfibril. Around 250 of these microfibrils form a fibril.

The fibrils are arranged in different layers (which can contain lignin and/or hemicellulose) to form a fibre. The individual fibres are bound together by lignin as well.

The pulps used in papermaking are often obtained by grinding the wood and an optional processing by heat and chemistry to remove undesired compounds from the cellulosic fibres.

The fibres are ground and cut to a certain fineness (depending on the desired properties). The grinding of the fibres is achieved with a refiner (such as a conic rotor-stator mill or disc- or double-disc refiners). The refiner also fibrillates the fibres on the surface which means that some fibrils are partially pulled out of the surface of the fibre. This leads to a better retention of, and, frequently, adhesion to, pigments, which may be added in paper production, and also to an enhanced potential of hydrogen bonding between the fibres of the paper. This results in improved mechanical properties. A side-effect is also that the paper becomes denser and more transparent because of a loss of light scattering as the size of the scattering centres moves away from the accepted optimum of half the wave length of light (glassine and greaseproof papers).

When fibres become refined under applied energy they become fibrillated as the cell walls are broken and torn into attached strips, i.e. into fibrils. If this breakage is continued to separate the fibrils from the body of the fibre, it releases the fibrils. The breakdown of fibres into microfibrils is referred to as "microfibrillation". This process may be continued until there are no fibres left and only fibrils of nano size (thickness) remain.

If the process goes further and breaks these fibrils down into smaller and smaller fibrils, they eventually become cellulose fragments or nano-gel. Depending on how far this last step is taken some nano-fibrils may remain amongst the nano-fibril gel. The breakdown to primary fibrils may be referred to as "nano-fibrillation", where there may be a smooth transition between the two regimes. The primary fibrils form in an aqueous environment a gel (meta stable network of primary fibrils) which may be referred to as "nano-fibrillar gel". The gel formed from the nano-fibrils can be considered to contain nanocellulose.

Nano-fibrillar gels are desirable as they usually contain very fine fibrils, considered to be constituted in part of nanocellulose, showing a stronger binding potential to themselves, or to any other material present, than do fibrils which are not so fine or do not exhibit nanocellulosic structure.

The achievable fineness with conventional refiners however is limited. Also, a number of other apparati for breaking down particles are not capable of breaking down cellulose fibres to nano-fibrils, such as fluffers mentioned in US 2001/0045264, which are only capable of separating given size fractions of fibres from each other.

Similarly, in WO 02/090651 a method for recycling pulp rejects generated during manufacturing of paper, paperboard or cardboard is described, wherein cleaner rejects containing among other things fibres, pigments and/or fibres are milled to a certain grain size by ball mills. However, no mention is made of the fibrillation of the fibres present, let alone the fibrillation into nano-fibrils or a nano-fibrillar cellulose gel.

If a further breakdown of the fibres into fibrils or even in cellulose molecules is desired, other methods are needed.

For example, in U.S. Pat. No. 4,374,702 a process for preparing microfibrillated cellulose is described comprising passing a liquid suspension of fibrous cellulose through a high pressure homogenizer having a small diameter orifice in which the suspension is subjected to a pressure drop of at least 3000 psi and a high velocity shearing action followed by a high velocity decelerating impact against a solid surface, repeating the passage of said suspension through the orifice until said cellulose suspension becomes a substantially stable suspension, said process converting said cellulose into microfibrillated cellulose without substantial chemical change of the cellulose starting material. A nano-fibrillar cellulose gel is not mentioned.

U.S. Pat. No. 6,183,596 B1 discloses a process for producing super microfibrillated cellulose by passing a slurry of a previously beaten pulp through a rubbing apparatus having two or more grinders which are arranged so that they can be rubbed together to microfibrillate the pulp to obtain microfibrillated cellulose and further super microfibrillate the obtained microfibrillated cellulose with a high-pressure homogenizer to obtain the super microfibrillated cellulose. There is however no mention of a nano-fibrillar cellulose gel.

Furthermore, ultra-fine friction grinders can be used, wherein the grinder reduces the fibres into fines by mechanical shearing (cf. e.g. U.S. Pat. No. 6,214,163 B1), which however does not automatically lead to a nano-fibrillar cellulose gel.

The mechanical production of nano-fibrillar cellulose is not trivial. For example, there is a problem of increasing viscosity during the fibrillation process. This can stop the process completely or increase the needed specific energy.

Thus, there is still a need for a process for producing nano-fibrillar cellulose gels, which is not only easily carried out, but energy efficient.

It is one objective of the present invention to provide such process for the production of nano-fibrillar cellulose gels.

It has now been found that in machines, where the throughput is a function of viscosity, an advantageous decrease of the viscosity of nano-fibrillar cellulose gels is observed by the addition and co-processing of certain fillers and/or pigments with the cellulose fibre containing pulp resulting in a better throughput.

Thus, the above problem is solved by the process for the production of nano-fibrillar cellulose gels of the present invention.

This process is characterized by the following steps:
(a) providing cellulose fibres;
(b) providing at least one filler and/or pigment;
(c) combining the cellulose fibres and the at least one filler and/or pigment;
(d) fibrillating the cellulose fibres in the presences of the at least one filler and/or pigment until a gel is formed.

Nano-fibrillar cellulose in the context of the present invention means fibres, which are at least partially broken down to primary fibrils. If these primary fibrils are in an aqueous environment, a gel (meta stable network of primary fibrils considered in the limit of fineness to be essentially nanocellulose) is formed, which is designated as "nano-fibrillar gel", wherein there is a smooth transition between nano fibres and nano-fibrillar gel, comprising nano-fibrillar gels containing a varying extent of nano-fibrils, all of which are comprised by the term nano-fibrillar cellulose gels according to the present invention.

In this respect, fibrillating in the context of the present invention means any process which predominantly breaks down the fibres and fibrils along their long axis resulting in the decrease of the diameter of the fibres and fibrils, respectively.

According to the process of the present invention, the fibrillation of cellulose fibres in the presence of at least one filler and/or pigment provides a nano-fibrillar cellulose gel. The fibrillation is performed until the gel is formed, wherein the formation of the gel is verified by the monitoring of the viscosity in dependence of the shearing rate. Upon step-wise increase of the shearing rate a certain curve reflecting a decrease of the viscosity is obtained. If, subsequently the shearing rate is step-wise reduced, the viscosity increases again, but the corresponding values over at least part of the shear rate range as shearing approaches zero are lower than when increasing the shearing rate, graphically expressed by a hysteresis in the of the viscosity plotted against the shearing rate. As soon as this behaviour is observed, a nano-fibrillar cellulose gel according to the present invention is formed.

Furthermore, during the fibrillation of the pulp in machines, where the throughput is a function of viscosity, the viscosity of the gel formed according to the present invention is preferably lower than the viscosity of a corresponding suspension of nano-fibrillar cellulose, having been fibrillated in the absence of fillers and/or pigments.

The Brookfield viscosity can be measured with any conventional Brookfield viscometer using routine operations known by the person skilled in the art.

Cellulose fibres, which can be used in the process of the present invention may be such contained in pulps selected from the group comprising eucalyptus pulp, spruce pulp, pine pulp, beech pulp, hemp pulp, cotton pulp, and mixtures thereof. In one embodiment, all or part of this cellulose fibre may be issued from a step of recycling a material comprising cellulose fibres. Thus, the pulp may also be recycled pulp.

The size of the cellulose fibres in principle is not critical. Useful in the present invention generally are any fibres commercially available and processable in the device used for their fibrillation. Depending on their origin, cellulose fibres may have a length of from 50 mm to 0.1 µm. Such fibres, as well as such having a length of preferably 20 mm to 0.5 µm, more preferably from 10 mm to 1 mm, and typically from 2 to 5 mm, can be advantageously used in the present invention, wherein also longer and shorter fibres may be useful.

It is advantageous for the use in the present invention that the cellulose fibres are provided in the form of a suspension, especially an aqueous suspension. Preferably, such suspensions have a solids content of from 0.2 to 35 wt-%, more preferably 0.25 to 10 wt-%, even more preferably 0.5 to 5 wt-%, especially 1 to 4 wt-%, most preferably 1.3 to 3 wt-%, e.g. 1.5 wt-%.

The at least one filler and/or pigment is selected from the group comprising precipitated calcium carbonate (PCC); natural ground calcium carbonate (GCC); dolomite; talc; bentonite; clay; magnesite; satinwhite; sepiolite, huntite, diatomite; silicates; and mixtures thereof. Precipitated calcium carbonate, which may have vateritic, calcitic or aragonitic crystal structure, and/or natural ground calcium carbonate, which may be selected from marble, limestone and/or chalk, are especially preferred.

In a special embodiment, the use of ultrafine discrete prismatic, scalenohedral or rhombohedral precipitated calcium carbonate may be advantageous.

The fillers and/or pigments can be provided in the form of a powder, although they are preferably added in the form of a suspension, such as an aqueous suspension. In this case, the solids content of the suspension is not critical as long as it is a pumpable liquid.

In a preferred embodiment, the filler and/or pigment particles have a median particle size of from 0.5 to 15 µm, preferably 0.7 to 10 µm, more preferably 1 to 5 µm and most preferably 1.1 to 2 µm, e.g. 1.5 µm or 3.2 µm.

Especially preferably, the filler and/or pigment particles have a median particle size of from 0.01 to 15 µm, preferably 0.1 to 10 µm, more preferably 0.3 to 5 µM and most preferably 0.5 to 4 µm.

For the determination of the weight median particle size $d_{50}$, for particles having a $d_{50}$ greater than 0.5 µm, a Sedigraph 5100 device from the company Micromeritics, USA was used. The measurement was performed in an aqueous solution of 0.1 wt-% $Na_4P_2O_7$. The samples were dispersed using a high-speed stirrer and ultrasound. For the determination of the volume median particle size for particles having a $d_{50} \leq 500$ nm, a Malvern Zetasizer Nano ZS from the company Malvern, UK was used. The measurement was performed in an aqueous solution of 0.1 wt % $Na_4P_2O_7$. The samples were dispersed using a high-speed stirrer and ultrasound.

The fillers and/or pigments may be associated with dispersing agents such as those selected from the group comprising homopolymers or copolymers of polycarboxylic acids and/or their salts or derivatives such as esters based on, e.g., acrylic acid, methacrylic acid, maleic acid, fumaric acid, itaconic acid, e.g. acryl amide or acrylic esters such as methylmethacrylate, or mixtures thereof; alkali polyphosphates, phosphonic-, citric- and tartaric acids and the salts or esters thereof; or mixtures thereof.

The combination of fibres and at least one filler and/or pigment can be carried out by adding the filler and/or pigment to the fibres in one or several steps. As well, the fibres can be added to the filler and/or pigment in one or several steps. The filler and/or pigment as well as the fibres can be added entirely or in portions before or during the fibrillating step. However, the addition before fibrillating is preferred.

During the fibrillation process, the size of the fillers and/or pigments as well as the size of the fibres can change.

Preferably, the weight ratio of fibres to fillers and/or pigments on a dry weight basis is from 1:33 to 10:1, more preferably 1:10 to 7:1, even more preferably 1:5 to 5:1, typically 1:3 to 3:1, especially 1:2 to 2:1 and most preferably 1:1.5 to 1.5:1, e.g. 1:1.

The dosage of filler and/or pigment may be critical. If there is too much of the filler and/or pigment, this may influence the formation of the gel. Thus, if no gel formation is observed in specific combination, it might be necessary to reduce the amount of filler and/or pigment.

Furthermore, in one embodiment, the combination is stored for 2 to 12 hours, preferably 3 to 10 hours, more preferably 4 to 8 hours, e.g. 6 hours, prior to fibrillating it, as this ideally results in swelling of the fibres facilitating the fibrillation.

Fibre swelling may be facilitated by storage at increased pH, as well as by addition of cellulose solvents like, e.g. copper(II)ethylenediamine, iron-sodium-tartrate or lithium-chlorine/dimethylacetamine, or by any other method known in the art.

Fibrillating is carried out by means of any device useful therefore. Preferably the device is a homogenizer. It may also be an ultra fine friction grinder as described in U.S. Pat. No. 6,214,163 or U.S. Pat. No. 6,183,596.

Suitable for the use in the present invention are any commercially available homogenizers, especially high pressure homogenizers, wherein the suspensions are pressed under high pressure through a restricted opening, which may comprise a valve, and are discharged from the restricted opening at high pressure against a hard impact surface directly in front of the restricted opening, thus reducing the particle size. The pressure may be generated by a pump such as a piston pump, and the impact surface may comprise an impact ring extending around the annular valve opening. Example for homogenizers which can be used in the present invention Ariete NS2006L of GEA Niro Soavi. However, inter alia, also homogenizers such as of the APV Gaulin Series, HST HL Series or the Alfa Laval SHL Series can be used.

Furthermore, devices such as ultra-fine friction grinders, e.g. a Super Mass Colloider, can be advantageously used in the present invention.

The present manufacturing process is especially advantageous with respect to its efficiency. As mentioned above, the known pulp suspensions or gels have the drawback to have a relatively high viscosity in the fibrillation process, often leading to a high energy consumption, which is undesirable from an economical as well as ecological point of view.

Generally, minimising the viscosity in the process allows for two benefits:
(i) the gel can be formed more efficiently, but, nonetheless, the viscosity will rise (on a lower level line) as the gel is formed progressively,
(ii) an even more beneficial gel can be made in viscosity critical processes by running with the invention until viscosity again rises close to the running maximum workable in the process, which means that the progress to ever finer gel has gone further than previously could be achieved.

Thus, the total energy to be applied for achieving a certain viscosity is significantly higher for gels containing the same type and amount of pulp as the nano-fibrillar cellulose gels according to the present invention, but do not contain filler and/or pigment. The same applies to gels or suspensions of the same kind and amount of pulp, but wherein the filler and/or pigment was added after fibrillation.

Consequently, the efficiency of the nano-fibrillar cellulose gel with respect to the total energy consumption in order to achieve a certain Brookfield viscosity is higher than the efficiency of a corresponding nano-fibrillar cellulose gel or suspension having been fibrillated in the absence of fillers and/or pigments or a corresponding gel or suspension not containing filler and/or pigment.

Thus, it is a further aspect of the invention to provide a process for enhancing the efficiency of producing nano-fibrillar cellulose gels by preparing the nano-fibrillar gels by a process as described above.

Another aspect of the present invention is the nano-fibrillar cellulose gel obtained by the processes according to the invention, the efficiency of which with respect to the total energy consumption in order to achieve a certain Brookfield viscosity preferably is higher than the efficiency of a corresponding nano-fibrillar cellulose gel having been fibrillated in the absence of fillers and/or pigments or a corresponding gel not containing filler and/or pigment.

Due to their mechanical strength properties the nano-fibrillar cellulose gels can be advantageously used in applications such as in material composites, plastics, paints, rubber, concrete, ceramics, adhesives, food, or in wound-healing applications.

The figures described below, and the examples and experiments, serve to illustrate the present invention and should not restrict it in any way.

EXAMPLES

A) Rheological Characterization

For exemplifying the present invention, highly refined pulp (standard eucalyptus pulp with 20° SR refined to 80-83° SR using a pulp refiner used in paper plants) and a mixture of this pulp with a defined amount of carbonate (100 wt-% based on the dry weight fibres present, dry on dry (d/d), was fibrillated using a homogenizer. The pulp (reference) and the mixture were homogenized for 10 hours at around 1 000 bar pressure and viscosity measurements and SEM pictures were taken at defined time intervals.

The viscosity (at 50° C.) of the reference of 560 mPa·s after 10 hours homogenizing could be decreased to 435 mPa·s by co-homogenizing with 100 wt-% calcium carbonate (Omyacarb 1 AV) based on the dry weight fibres present.

In order to check whether the addition of calcium carbonate alone leads to a decrease of the viscosity of the homogenized pulp or the co-homogenizing is necessary, a sample of already homogenized pulp was mixed with calcium carbonate (100 wt-% calcium carbonate based on the dry weight fibres present, d/d), which is referred to as blend.

The viscosity of the "blend" (865 mPa·s) was higher than the viscosity of the co-homogenized mixture (435 mPa·s) and even higher than the viscosity of the homogenized reference (560 mPa·s) without calcium carbonate present.

Carbonate slurries with the same solids content but without homogenized pulp, on the other hand, do not show a significantly higher viscosity than the fibre-containing samples.

2. Material

Carbonate: Omyacarb 1 AV (GCC, solids content 100 wt % based on weight of fibres present, weight median particle size $d_{50}=1.7$ μm measured by Sedigraph 5100) available from Omya AG Pulp: Standard eucalyptus pulp (20° SR) fibrillated to 80-83° SR using a refiner used in paper plants. The Schopper-Riegler degree (°SR) was measured according to the Zellcheming Merkblatt V/7/61 and standardized in ISO 5267/1.

3. Experimental Setup 3.1 Sample Preparation

For one homogenizer long term trial 1 000 g (solids content of about 3 wt-%) of the pulp as received was mixed with 1 250 g tap water using a stirrer (dissolver disc operating a rotation speed of 4 000 rpm) resulting in a solids content of about 1.3 wt-%. If necessary, the corresponding amount of calcium carbonate (Omyacarb 1 AV) was added while stirring further (cf. table 1). According amounts of this slurry were taken to perform viscosity experiments and SEM micrographs as described below. The rest of the slurry was transferred in the reservoir of the homogenizer. The samples which were used for the viscosity measurements were recycled in the process after performing the measurements.

TABLE 1

| Sample. No. | Calcium Carbonate | Amount [wt-%, d/d] | Starting solids content [wt-%] | Final solids content [wt-%] | Total time in homogenizer [h] |
|---|---|---|---|---|---|
| 1 | Omyacarb 1 AV | 0 | 1.3 | 1.7 | 10 |
| 2 | Omyacarb 1 AV | 100 | 2.6 | 2.4 | 10 |

3.2 Homogenizer

A homogenizer (GEA Niro Soavi; type NS 2006 L) was used for the fibrillation experiments. The reservoir was stirred with an external double propeller stirrer to prevent sedimentation of the slurry and to maintain a good conversion.

The machine was started with no pressure applied (the pistons on both homogenizing stages were completely pulled back) and the lowest pumping velocity. For adjusting the pressure of about 1 000 bar only the piston of the first stage was pushed in. The reaction time started when a pressure of 1 000 bar was achieved, wherein fluctuations of the pressure by ±200 bar were observed. Consistent under- or overpressure was compensated for by changing the position of the piston.

The slurry was held in circulation. Samples were taken out after the homogenizing chamber (before entering the reservoir again) to ensure at least one passage of the fibres through the homogenizing chamber.

4. Methods 4.1 Viscosity Measurements 4.1.1 Brookfield Viscosity

The viscosity measurements were performed on a Brookfield DV-II+ viscometer. The motor speed was set to 100 rpm and the viscosity was read out after 10, 60 and 600 seconds. The samples were measured either at room temperature or at 50° C. The samples were heated in a thermally controlled ultrasonic bath.

4.1.2 Rheology Measurements

Rheological measurements were performed using a Paar-Physika MCR 300 with the CC28.7 measuring system. The samples were measured at 20° C.

4.2 SEM

The scanning electron micrographs (SEM) were obtained by adding 0.5 g samples to 200 cm$^3$ distilled water which then was filtered through a 0.8 μm pore nitrocellulose filter. The filter with overlying sample was dried in a vacuum drier. Preparations obtained on the membrane filter in this way were sputtered with 50 nm gold and evaluated in the SEM at various magnifications.

5. Results 5.1 Viscosity Measurements

Figure 1:
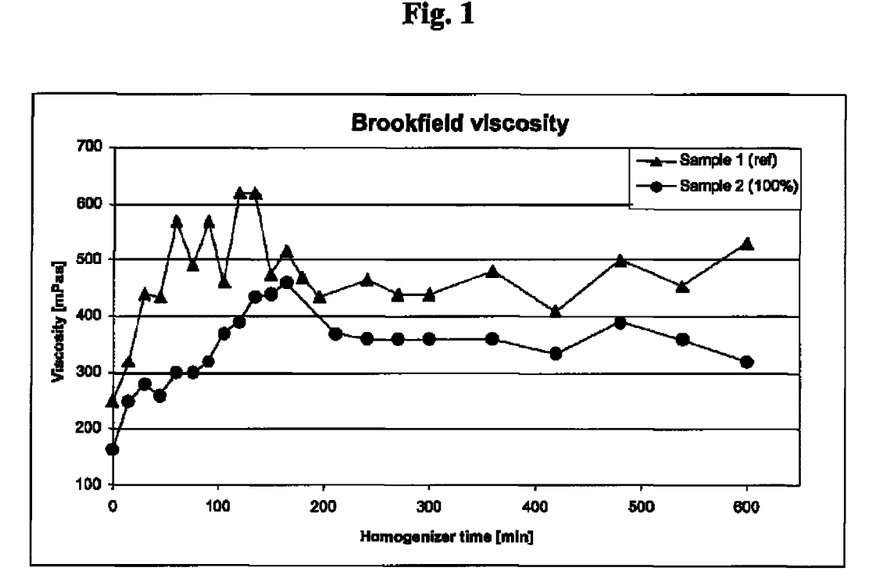
FIG. 1 shows the Brookfield viscosity progression during homogenizing of pulp mixtures with and without calcium carbonate.

From FIG. 1 the evolution of the viscosity (Brookfield) during homogenizing can be taken. The viscosity was read out after 600 seconds. The samples were measured at about 35° C. (which was the temperature of the samples taken directly after the homogenization chamber). Sample 1 is only pulp and therefore used as reference material for the calcium carbonate containing sample 2. As already mentioned, the viscosity increases during fibrillation. As can be seen, sample 2 containing 100 wt-% calcium carbonate (based on the dry weight fibres present; d/d) always had a lower viscosity than the reference, but also increases with increasing homogenization time.

For verifying whether the presence of calcium carbonate is necessary during the homogenizing for lowering the viscosity, also a blend of homogenized (10 h) sample 1 and 100 wt-% calcium carbonate (based on the dry weight fibres present; d/d) added after homogenization was produced and investigated. The viscosity was read out after 10, 60 and 600 seconds. The samples were heated in a thermally controlled ultrasonic bath and measured at 50° C.

Figure 2:
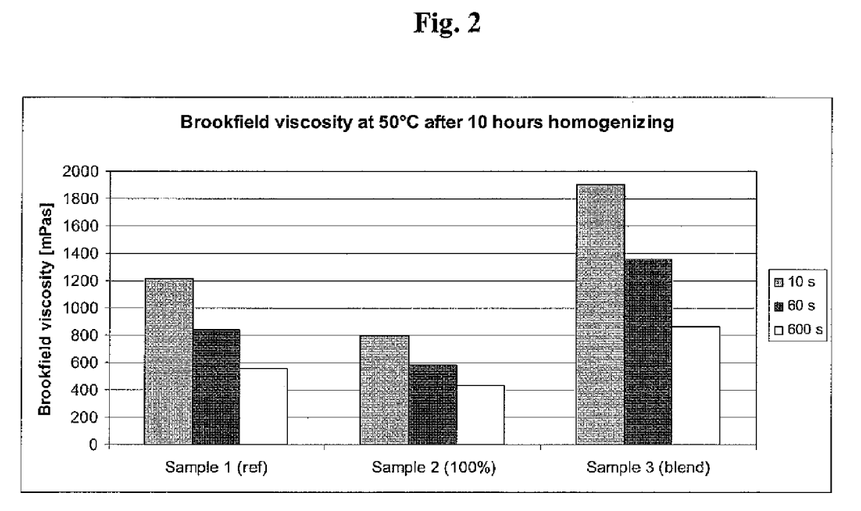
FIG. 2 shows the Brookfield viscosity of pulp mixtures with and without calcium carbonate, added before or after homogenization.

FIG. 2 shows the viscosities of pure homogenized pulp (sample 1), and pulp co-homogenized with 100 wt-% calcium carbonate (based on the dry weight fibres present; d/d) (sample 2), and mixtures of homogenized pulp and 100 wt-% calcium carbonate (based on the dry weight fibres present; d/d) added after homogenization (blend). In this respect, "10 s", "60 s" and "600 s" refer to the values of the Brookfield viscosity taken after 10, 60 and 600 seconds after the "power on" of the motor.

As can be seen, the co-homogenized mixture has a lower viscosity than the reference, whereas the blend has a higher viscosity than the corresponding co-homogenized mixture (sample 2) and the reference (sample 1).

Comparing the final viscosities (at 10 h homogenizing time) in FIG. 1 and in FIG. 2, slightly different values can be seen. This difference is accredited to the temperature dependence of the viscosity of the pulp mixtures.

5.2 Rheology Measurements

Figure 3:
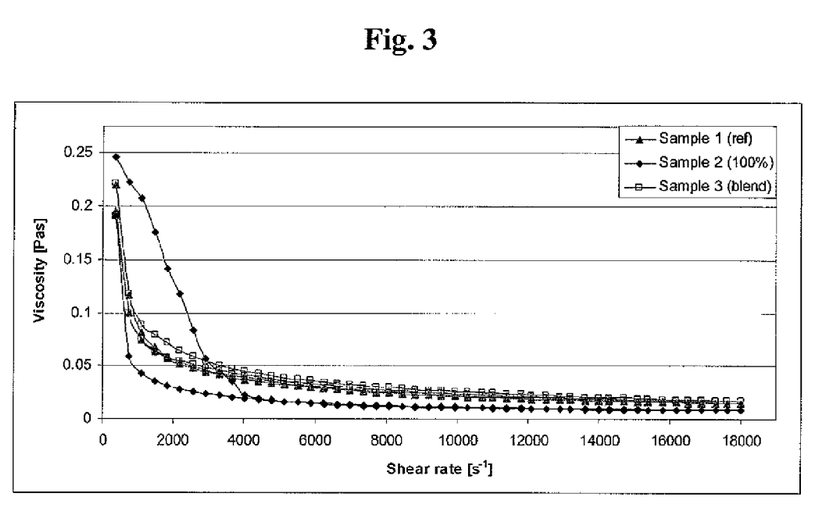
FIG. 3 shows the dependence of the viscosity of pulp mixtures with and without calcium carbonate added before or after homogenization on the shearing rate.

As one can see in FIG. 3, all the samples show a shear thinning behaviour. Table 2 shows the viscosities of the reference and the 100 wt-% calcium carbonate co-homogenized mixture and a 100 wt-% blend at 18 000 s$^{-1}$. Similar to the data of the Brookfield measurements (FIG. 2), the 100 wt-% carbonate co-homogenized has the lowest viscosity (8 mPa·s) and the 100 wt-% carbonate blend the highest viscosity (17 mPa·s).

TABLE 2

| Sample | Viscosity [mPa · s] at 18 000 s$^{-1}$ |
|---|---|
| Sample 1 (ref) | 14 |
| Sample 2 (co-homogenized with 100 wt.-% carbonate) | 8 |
| Sample 3 (blend with 100 wt.-% carbonate) | 17 |

Furthermore, it can clearly be taken from FIG. 3 that there is a hysteresis in the case of sample 2, representing the case of fibres co-homogenized with 100 wt.-% calcium carbonate.

At low shearing rates, the viscosity decreases progressively as shear is increased until a shearing rate of about 18 000 s$^{-1}$. Upon subsequently slowly decreasing the shearing rates, lower viscosities can be observed than at the corresponding shearing rates in the previous increasing step, wherein the viscosity now always remains lower than the viscosities in the previous step, and lower than the viscosity of the blend and the pulp only sample 1 under similar shear conditions.

This behaviour not only shows the low viscosities, which can be achieved according to the invention, but also is a clear indication of the foimation of a gel.

5.3 SEM

Figure 4A:
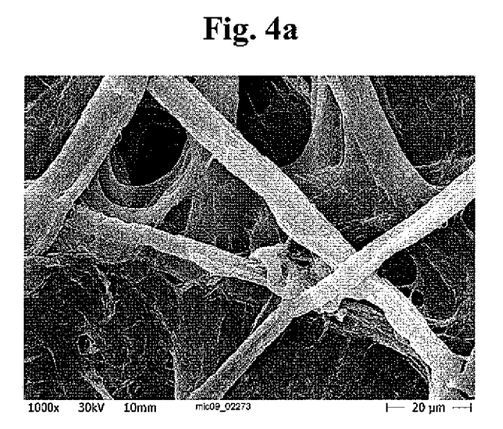
FIGS. 4a and b show SEM images of only fibres (FIG. 4a), fibres and 100 wt.-% calcium carbonate based on weight of fibres present before homogenization (FIG. 4b).
Figure 4B:
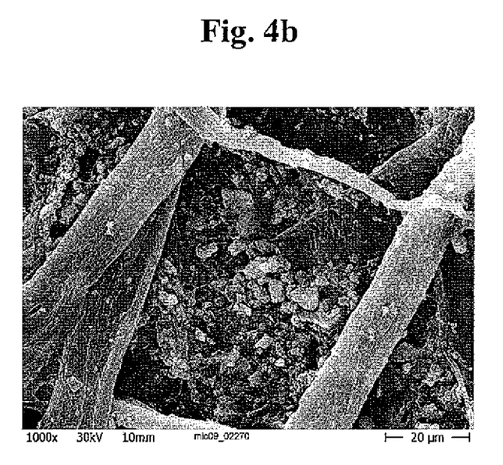
Figure 5A:
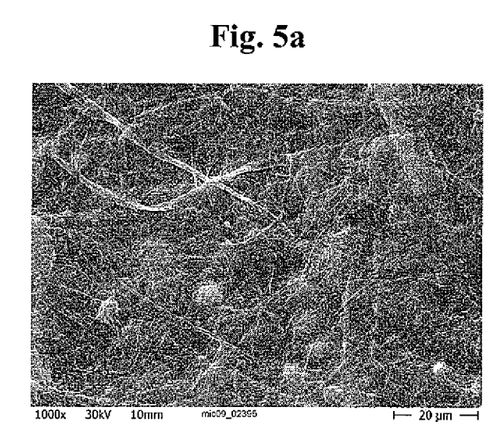
FIGS. 5a and b show SEM images of only fibres (FIG. 5a), fibres and 100 wt.-% calcium carbonate based on weight of fibres present after 2 hours of homogenization (FIG. 5b).
Figure 5B:
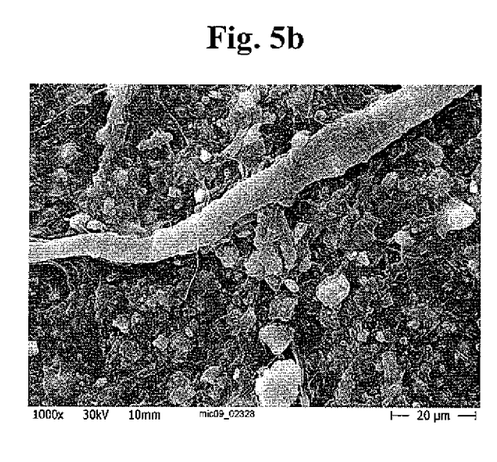
Figure 6A:
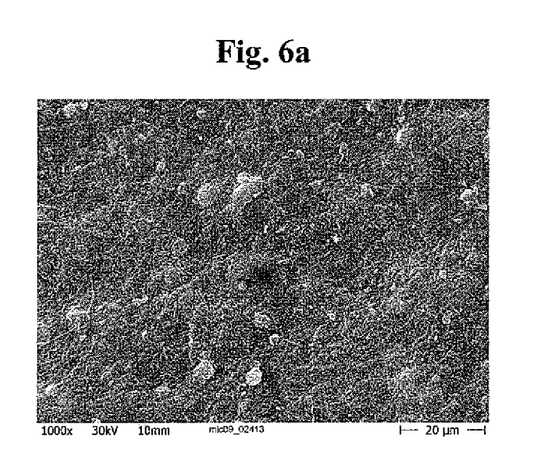
FIGS. 6a and 6b show SEM images of only fibres (FIG. 6a), fibres and 100 wt.-% calcium carbonate based on weight of fibres present after 10 hours of homogenization (FIG. 6b).
Figure 6B:
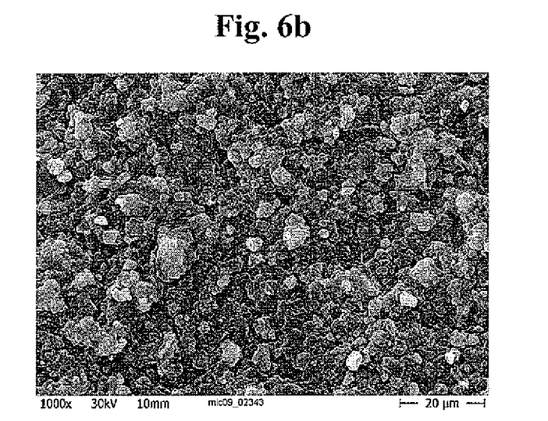
Figure 7:
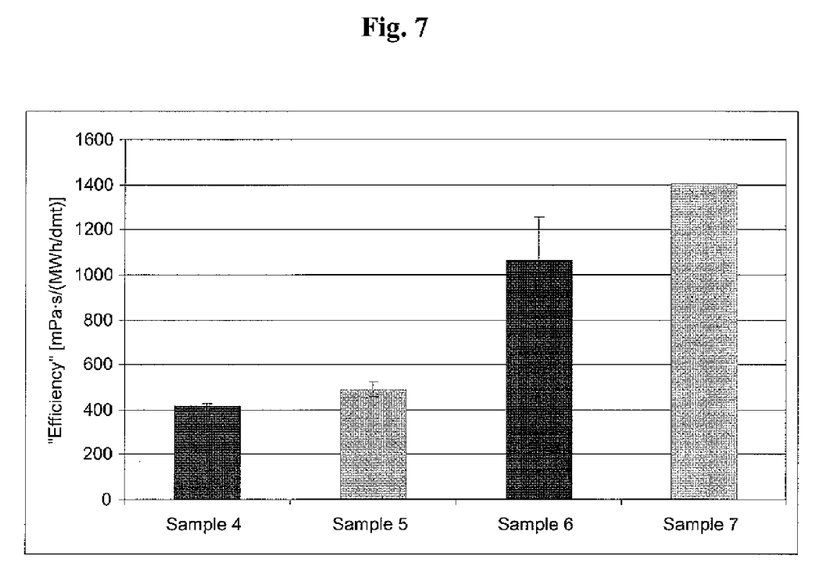
FIG. 7 shows the efficiency of gel formation of mixtures with and without calcium carbonate fillers.

Comparing FIG. 4a (referring to sample 1) and FIG. 4b (referring to sample 2) before homogenization, respectively, with FIGS. 5a and 5b after 2 hours homogenizing, respectively, and FIGS. 6a and 6b after 10 hours homogenizing, respectively, it can be seen that the pulp fibres become finer with increasing homogenizing time, and, without wishing to be bound to this theory, it appears that after a certain fineness of the fibrils is achieved they wrap around the carbonate particles and form a kind of layer on top of the carbonate particles.

B) Efficiency of Gel Formation

"Efficiency" in the context of the present invention is defined as the Brookfield viscosity (higher Brookfield viscosity means a more stable gel that means higher degree of fibrillation) achieved per specific energy consumption:

1. Processing

All Examples (samples 4-9) were processed with an ultrafine friction grinder (Supermasscolloider from Masuko Sangyo Co. Ltd, Japan (Model MKCA 6-2) with mounted silicon carbide stones having a grit class of 46 (grit size 297-420 μm). The gap between the stones was adjusted to "−50" μm (dynamic 0-point, as described in the manual delivered by the supplier). The speed of the rotating grinder was set to 2500 rpm for passes 1-5, to 2000 rpm for passes 6 and 7, to 1500 rpm for passes 8 and 9, to 1000 rpm for passes 10 and 11, to 750 rpm for passes 12 and 13 and to 500 rpm for passes 14 and 15.

2. Energy Measurement

The Energy measurement was performed by installing an electric meter (ELKO Syteme AG, DIZ D665Di) between the main power supply and the transformer to measure the energy take up of the whole Supermasscolloider system (as delivered from the supplier). The electric meter sends one signal per Wh to a digital counter (Hengstler, tico 731) to be able to read out the energy consumption per pass at the end of a pass with an accuracy of one Wh.

3. Weight Measurements

The solids content was measured using a Mettler Toledo HB 43-S Halogen solids balance. The end total mass was measured using a Mettler PK 36 Delta Range balance. The initial dry mass is the sum of all dry weight-ins at the beginning of an experiment (detailed compositions can be found in the formulations of the single experiments)

4. Brookfield Viscosity Determination

Brookfield viscosity was measured with Brookfield Model DV-II+ Viscometer.

To have a better comparability of the Brookfield measurement data, the Brookfield viscosity was measured in a dilution row to calculate the Brookfield viscosity at a fixed solids content. Additionally it was defined that only the ratio of dry cellulosic content (originating from dry pulp) to water is taken as reference parameter for Brookfield viscosity. The following formula was used to calculate the cellulosic solids content (s.c.$_c$):

$$s.c._c = \frac{\frac{s.c.}{p_c + p_f}}{100 - \left(p_f \cdot \frac{s.c.}{p_c + p_f}\right)}$$

s.c.$_c$: cellulosic solids content
s.c.: measured solids content of a sample
p$_c$: part cellulosic content, per definition=1
p$_f$: parts filler, weight ratio to part cellulosic content The standardized Brookfield viscosity BV$_{2\%}$ was determined by the following method:

1. The solids content and the Brookfield viscosity (100 rpm, measuring after 30 s) of the original product are measured.
2. Three dilutions of the original products are produced by adding according amounts of tap water of which the solids contents (weight in at least 10 g) and the Brookfield viscosities (100 rpm, measuring after 30 s) are measured.
3. An xy-scatter diagram (x: solids content, y: Brookfield viscosity) is made and the points are fitted with a power law curve (y=ax$^b$).
4. Use the parameters a and b to calculate the Brookfield viscosity at the standardized cellulosic solids content x$_s$ of 2 wt %

To correct the intrinsic influence of Omyacarb 1 AV (samples 5-7) on the Brookfield viscosity of gels, a comparative gel containing no filler (sample 4) was mixed with according amounts of Omyacarb 1 AV (to have similar ratios as in samples 5-7). The BV$_2$% of these mixtures was determined according to the above mentioned procedure and percentage corrections with reference to the gel containing no filler were calculated. The percentage corrections are: for 0.1 p (part by weight; did; cf. sample 5) filler: <0.1% (neglected), 3 p (parts by weight; d/d; cf. sample 6) filler: −14.5%, 10 p (part by weight; d/d; cf. sample 7) filler: −37.5%.

According corrections for samples 8 and 9 were not performed, such that the presented "efficiency" values described below will be overestimated in a range of about 15 to 20%)

5. Calculation of Specific Energy Consumption

The specific energy consumption per pass E$_n$ is calculated as follows:

$$E_n = \frac{E_n}{m_n}$$

$$m_n = m_1 - \frac{n}{14}(m_1 - m_{15})$$

$$m_{15} = \sigma \cdot M$$

$E_n$: specific energy of pass n[MWh/dmt]
$E_n$: measured energy of pass n[Wh]
$m_n$: dry mass of pass n[g]
$m_1$: initial dry mass [g]
$m_{15}$: end dry mass [g]
n: pass number
σ: solids content of final mass [wt %]
M: final total mass [g]

6. Calculation of "Efficiency"

"Efficiency" (ε) in the context of the present invention is defined as the Brookfield viscosity (higher Brookfield viscosity means a more stable gel that means higher degree of fibrillation) achieved per specific energy consumption:

$$\varepsilon = \frac{BV_{2\%}}{E_{1-15}}$$

ε: "Efficiency"

$$\left[\frac{mPas}{MWh/dmt}\right]$$

$BV_2\%$: Brookfield viscosity at 2 wt % solids [mPas]
$E_{1-15}$: Total specific energy of one example[MWh/dmt]

7. Material

Omyacarb 1 AV: available from Omya AG; Fine calcium carbonate powder, manufactured from a high purity white marble; The weight median particle size $d_{50}$ is 1.7 μm measured by Sedigraph 5100.

Nano GCC: Natural ground calcium carbonate (marble from Vermont); Dispersed slurry (solids content 50 wt %); The volume median particle size $d_{50}$ is 246 nm measured by Malvern Zetasizer Nano ZS.

Finntalc F40: Finntalc F40 available from Mondo Minerals; Talc filler for paper and board.

Eucalyptus pulp: Dry mat, brightness: 88.77%, 17° SR
Pine pulp: Dry mat, brightness: 88.19%, 20° SR 8. Sample Preparation Sample 4 (Comparative):
180 g dry Eucalyptus pulp and 5820 g tap water were mixed using a Pendraulik stirrer at 2000 rpm with a mounted dissolver disk (d=70 mm) for at least 10 minutes. This mixture was processed with the Supermasscolloider as described above in the according paragraph. This example was performed three times to show its reproducibility.

Sample 5:
180 g dry Eucalyptus pulp, 5820 g tap water and 18 g Omyacarb 1 AV (10:1 pulp to filler, dry/dry) were mixed using a Pendraulik stirrer at 2000 rpm with a mounted dissolver disk (d=70 mm) for at least 10 minutes. This mixture was processed with the Supermasscolloider as described above in the according paragraph. This example was performed three times to show its reproducibility.

Sample 6:
180 g dry Eucalyptus pulp, 5820 g tap water and 540 g Omyacarb 1 AV (1:3 pulp to filler, dry/dry) were mixed using a Pendraulik stirrer at 2000 rpm with a mounted dissolver disk (d=70 mm) for at least 10 minutes. This mixture was processed with the Supermasscolloider as described above in the according paragraph. This experiment was performed two times to show its reproducibility.

Sample 7:
180 g dry Eucalyptus pulp, 5820 g tap water and 1800 g Omyacarb 1 AV (1:10 pulp to filler, dry/dry) were mixed using a Pendraulik stirrer at 2000 rpm with a mounted dissolver disk (d=70 mm) for at least 10 minutes. This mixture was processed with the Supermasscolloider as described above in the according paragraph.

Sample 8:
180 g dry Pine pulp, 5820 g tap water and 180 g Finntalc F40 (1:1 pulp to filler, dry/dry) were mixed using a Pendraulik stirrer at 2000 rpm with a mounted dissolver disk (d=70 mm) for at least 10 minutes. This mixture was processed with the Supermasscolloider as described above in the according paragraph.

Sample 9:
180 g dry Eucalyptus pulp, 5820 g tap water and 360 g Nano GCC (1:1 pulp to filler, dry/dry) were mixed using a Pendraulik stirrer at 2000 rpm with a mounted dissolver disk (d=70 mm) for at least 10 minutes. This mixture was processed with the Supermasscolloider as described above in the according paragraph.

9. Results

Samples 4-7:
When comparing samples 4-7 it is obvious that the efficiency increases for gels that were produced in the presence of more filler, namely by up to 250%. The efficiency gain has to be more than 15% compared to a gel that was formed in the absence of filler.

Samples 8 and 9:
Samples 8 and 9 did not undergo the Brookfield viscosity-correction due to the intrinsic Brookfield viscosity increase of filler addition (see section "Brookfield viscosity determination").

Figure 8:
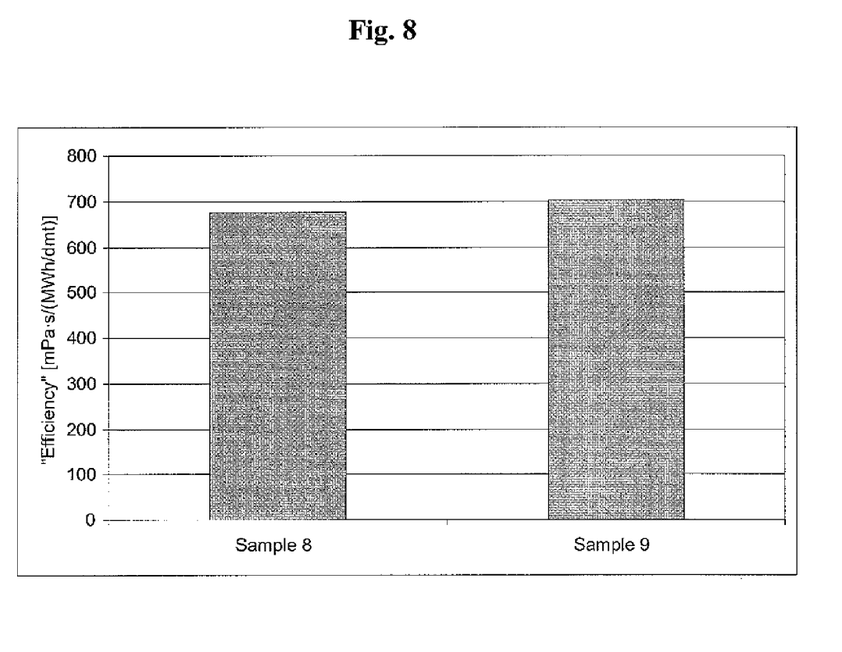
FIG. 8 shows the efficiency of gel formation of mixtures containing nanometer-sized calcium carbonate and talc as fillers.

However, as can be taken from FIG. 8, the efficiency is about 75% higher than the one of comparative sample 4, and still 40% higher if a correction of minus 20% of the measured efficiency value is assumed.

The invention claimed is:

1. A process for the production of a nano-fibrillar cellulose gel comprising the steps of:
   (a) providing cellulose fibres;
   (b) providing a filler;
   (c) combining the cellulose fibres of step (a) and the filler of step (b); and
   (d) fibrillating the cellulose fibres and the filler from step (c) until a nano-fibrillar cellulose gel is formed,
   wherein the filler is calcium carbonate, and wherein in step (d) the weight ratio of fibres to filler on a dry weight basis is from 1:33 to 10:1.

2. The process according to claim 1, wherein the Brookfield viscosity of the nano-fibrillar cellulose gel formed in step (d) is lower than the Brookfield viscosity of a corresponding nano-fibrillar cellulose suspension having been fibrillated in the absence of the filler.

3. The process according to claim 1, wherein the cellulose fibres in step (a) are eucalyptus pulp, spruce pulp, pine pulp, beech pulp, hemp pulp, cotton pulp, or any mixture thereof.

4. The process according to claim 1, wherein the cellulose fibres in step (a) are provided in the form of a suspension.

5. The process according to claim 1, wherein the cellulose fibres in step (a) are provided in the form of a suspension at a solids content of from 0.2 to 35 wt-%.

6. The process according to claim 1, wherein the cellulose fibres in step (a) are provided in the form of a suspension at a solids content of from 0.25 to 10 wt-%.

7. The process according to claim 1, wherein the cellulose fibres in step (a) are provided in the form of a suspension at a solids content of from 0.5 to 5 wt-%.

8. The process according to claim 1, wherein the cellulose fibres in step (a) are provided in the form of a suspension at a solids content of from 1 to 4 wt-%.

9. The process according to claim 1, wherein the cellulose fibres in step (a) are provided in the form of a suspension at a solids content of from 1.3 to 3 wt-%.

10. The process according to claim 1, wherein the filler and/or pigment in step (b) is precipitated calcium carbonate.

11. The process according to claim 1, wherein the filler in step (b) is precipitated calcium carbonate having a vateritic, a calcitic or an aragonitic crystal structure.

12. The process according to claim 1, wherein the filler in step (b) is ultrafine discrete prismatic, scalenohedral or rhombohedral precipitated calcium carbonate.

13. The process according to claim 1, wherein the filler in step (b) is natural ground calcium carbonate.

14. The process according to claim 1, wherein the filler in step (b) is natural ground calcium carbonate selected from marble, limestone and/or chalk.

15. The process according to claim 1, wherein the filler in step (b) is in the form of particles having a medium particle size of from 0.01 to 15 µm.

16. The process according to claim 1, wherein the filler in step (b) is in the form of particles having a medium particle size of from 0.1 to 10 µm.

17. The process according to claim 1, wherein the filler in step (b) is in the form of particles having a medium particle size of from 0.3 to 5 µm.

18. The process according to claim 1, wherein the filler in step (b) is in the form of particles having a medium particle size of from 0.5 to 4 µm.

19. The process according to claim 1, wherein the filler in step (b) comprises a dispersing agent.

20. The process according to claim 19, wherein the dispersing agent is selected from homopolymers or copolymers of polycarboxylic acids and/or their salts or esters, acrylic acid, methacrylic acid, maleic acid, fumaric acid, itaconic acid, acryl amide or acrylic esters, or mixtures thereof alkali polyphosphates, phosphonic-, citric- and tartaric acids, salts or esters thereof or mixtures thereof.

21. The process according to claim 1, wherein in step (d) the weight ratio of fibres to filler on a dry weight basis is from 1:10 to 7:1.

22. The process according to claim 1, wherein in step (d) the weight ratio of fibres to filler on a dry weight basis is from 1:5 to 5:1.

23. The process according to claim 1, wherein in step (d) the weight ratio of fibres to filler on a dry weight basis is from 1:3 to 3:1.

24. The process according to claim 1, wherein in step (d) the weight ratio of fibres to filler on a dry weight basis is from 1:2 to 2:1.

25. The process according to claim 1, wherein in step (d) the weight ratio of fibres to filler on a dry weight basis is from 1:1.5 to 1.5:1.

26. The process according to claim 1, wherein the fibrillating in step (d) is carried out by a homogenizer or an ultra fine friction grinder.

27. A process for the production of a nano-fibrillar cellulose gel comprising the steps of:
(a) providing cellulose fibres;
(b) providing a filler;
(c) combining the cellulose fibres of step (a) and the filler of step (b); and
(d) fibrillating the cellulose fibres and the filler from step (c) until a nano-fibrillar cellulose gel is formed,
wherein the filler comprises calcium carbonate and one or more of dolomite, talc, bentonite, clay, magnesite, satin white, sepiolite, huntite, diatomite, and a silicate, and wherein in step (d) the weight ratio of fibres to filler on a dry weight basis is from 1:33 to 10:1.

* * * * *